US006875723B2

(12) United States Patent
Johansen et al.

(10) Patent No.: US 6,875,723 B2
(45) Date of Patent: Apr. 5, 2005

(54) PROCESS FOR THE PRODUCTION OF IRON OXIDE CONTAINING CATALYSTS

(75) Inventors: Keld Johansen, Frederikssund (DK); Petru Gordes, Hørsholm (DE)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 10/265,257

(22) Filed: Oct. 7, 2002

(65) Prior Publication Data

US 2003/0073574 A1 Apr. 17, 2003

(51) Int. Cl.$^7$ ................................. B01J 23/78
(52) U.S. Cl. ................. 502/306; 502/307; 502/314; 502/316; 502/328; 502/329; 502/330; 502/331
(58) Field of Search ................. 502/305, 307, 502/313–316, 318–319, 326, 329, 331, 337–338, 343, 345; 423/593, 594, 595, 600, 604, 607, 622, 626, 632, 658.5, 659

(56) References Cited

U.S. PATENT DOCUMENTS

| | | | | |
|---|---|---|---|---|
| 4,138,368 A | * | 2/1979 | Kiyomiya et al. | 502/312 |
| 4,316,736 A | * | 2/1982 | Van Hijfte et al. | 71/59 |
| 4,482,645 A | | 11/1984 | Jennings et al. | |
| 4,483,942 A | * | 11/1984 | Sekido et al. | 502/255 |
| 4,490,479 A | * | 12/1984 | Vogel et al. | 502/309 |
| 5,124,295 A | * | 6/1992 | Nebesh et al. | 502/64 |
| 5,176,888 A | * | 1/1993 | Stiles | 423/239.1 |
| 5,360,778 A | * | 11/1994 | Davis et al. | 502/202 |
| 5,565,091 A | * | 10/1996 | Iino et al. | 208/216 R |
| 5,856,261 A | * | 1/1999 | Culross et al. | 502/325 |
| 5,925,590 A | * | 7/1999 | White et al. | 502/302 |

FOREIGN PATENT DOCUMENTS

| | | |
|---|---|---|
| EP | 0 796 827 A | 9/1997 |
| EP | 0 836 881 A | 4/1998 |
| EP | 1 122 214 A | 8/2001 |
| EP | 1 223 164 A | 7/2002 |
| GB | 1 373 280 A | 11/1974 |
| WO | WO 01/28986 | 4/2001 |

* cited by examiner

Primary Examiner—Stuart Hendrickson
(74) Attorney, Agent, or Firm—Dickstein Shapiro Morin & Oshinsky LLP

(57) ABSTRACT

A process for the production mixed metal oxide containing catalysts comprising the steps of:

dissolution of metals Me=Fe, Ni, Al, Cu, Co, Zn, Cr, in nitric acid providing an acid solution of metal mixed nitrate products, aluminium can be added either as nitrate or hydroxide;

addition of a carbonhydrate, an amino acid and/or a carboxylic acid;

decomposition at 250–700° C. with free air supply of the acid solution by spraying onto the inner surface of one or more rotary kilns, into a spray calcination fluid bed, into a tower kiln or into a steel band conveyor furnace to iron oxide and $NO_x$; and optionally regeneration of the formed $NO_x$ to concentrated nitric acid and recycling of produced nitric acid to the first step.

1 Claim, No Drawings

PROCESS FOR THE PRODUCTION OF IRON OXIDE CONTAINING CATALYSTS

The present invention relates to a process for the production of metal oxide being useful for the preparation of mixed metal oxide catalysts.

BACKGROUND OF THE INVENTION

The state of the art methods for preparing mixed metal oxide include use of process by precipitation. Metal sulphate is a cheap pure raw material and good catalysts can be obtained by coprecipitation, but with a too high sulphur level. On the other hand, metal nitrate is an expensive raw material, and dissolving metals in nitric acid require the expensive nitric acid.

The known methods for preparing mixed metal oxide catalysts are costly in terms of purchasing the acid and basic raw materials and after the precipitation, washings and waste-water treatment.

This is described in U.S. Pat. No. 4,482,645, where Jennings et al. prepare a solution of iron nitrate and chromium nitrate, to which sodium carbonate is added and the formed iron and chromium hydroxides are washed before drying and decomposition to oxides.

The general object of this invention is, thus, to provide an improved process for the production of mixed metal oxide containing catalysts by simplified and inexpensive steps. Now an alternative manufacturing route based on metals via nitrates and nitric acid recovery has been invented and developed.

Compared to the known methods, the advantages of the invention include a high quality catalyst, and furthermore, high product yield through reduced loss of material during the processing.

SUMMARY OF THE INVENTION

The process of this invention comprises the following steps involving the metals Me=Co, Zn, Fe, Ni, Cr and/or Cu:

(a) Dissolution of Me in nitric acid providing an acid solution of (exemplified by a valence 3 metal) $Me(NO_3)_3$ by reaction (i):

$$2Me + 8HNO_3 \rightarrow 2\,Me(NO_3)_3 + 2\,NO + 4H_2O$$

(b) Optionally mixing of different metal nitrate solutions, e.g. $Fe(NO_3)_3$ solution with $Co(NO_3)_3$ solution. Aluminium is added either as nitrate or hydroxide.

(c) Optionally, addition of promoters. If promoters (PR) as PR=Na, K, Cs, Rb, Mg, Ca, Ba, Sr are desired in the final product, they are added as metal nitrates, carbonates, hydroxides etc to the dissolved Me(III) nitrate. The promoters are preferably added in the ratio range on molar base <PR/Me<0.2.

The final solution will be $Me(NO_3)_3$ solution, optionally containing promoters' PR nitrates.

The $HNO_3$ consumption will increase if $NO_2$ is formed.

(d) Thermal decomposition of the combined metal nitrate solution and promoter acid nitrate solution into mixed metal oxide $Me_2O_3$ or hydroxyoxide MeOOH optionally containing the promoters as oxides or nitrates depending on the chemical nature of the promoter. $NO_x$ gases are also formed during the reaction. The reaction for the pure decomposition of $Me(NO_3)_3$ will be as reaction (ii):

$$2Me(NO_3)_3 \rightarrow Me_2O_3 + 6NO_2 + 1.5O_2$$

(e) Optionally regeneration of $NO_x$ gases from reaction (i) and (ii) in one or in a series of absorption towers to more or less concentrated nitric acid according to reaction (iii):

$$6NO_2 + 3\,H_2O + 1.5O_2 \rightarrow 6HNO_3$$

or for NO (iv)

$$2NO + H_2O + 1.5O_2 \rightarrow 2HNO_3$$

Then the overall reaction for iron alone, i.e. when (i), (ii), (iii) and (iv) are combined, is:

$$\text{Total: } 2Me + 1.5O_2 \rightarrow Me_2O_3$$

When only the synthesis of the main component $Me_2O_3$ is considered, we see that for the total reaction no by-product is formed and the other raw material, oxygen, is taken from the air via the absorption towers.

The total reaction is somewhat influenced when promoters are included in the mixed metal nitrate solution. The influence is dependent on whether the promoter PR is added as nitrate, hydroxide, oxide etc. If it for example is added as $KNO_3$ with the molar ratio of K/Me=0.01 to total reaction scheme will be:

$$2Me + 1.5O_2 + 0.02KNO_3 + 0.01H_2O \rightarrow Me_2O_3 + 0.01K_2O + 0.02HNO_3.$$

This results in a slight formation of $HNO_3$ that can be used as dissolution.

NO and $NO_2$ or generally $NO_x$ being formed in the above reactions (i) and (ii) is converted into nitric acid again in absorption towers. Reactions (iii) and (iv) result in formation of nitric acid that is recycled and utilised for dissolution of Me, which is the main raw material in the process.

Though, due to minor loss of the nitric acid, occasionally small amounts of nitric acid have to be added to the regenerated acid in order to maintain or enhance dissolution of the raw material.

Decomposition in the above step (d) may be performed by spraying the acidic solution from step (a), (b) or (c) onto the inner surface of one or more rotary kilns, into spray calcination fluid beds, into a steel band conveyor furnace or into a tower falling particles kiln with free supply of air at 250–700° C. However, by using these methods, measures may be taken in order to prevent sticking of the product to the inner surface of the rotary kiln, e.g. by means of one or more sliding chains.

Adhesion of the prepared material from the decomposed acid solution to the inner side of said furnaces or kilns might also be prevented by other physical or chemical means.

The metal oxide product is further improved by minor addition of an organic compound capable of reducing nitrates. The reaction between the organic compound and the nitrate will then generate a faster decomposition of the nitrates. Furthermore, the powder is weakly agglomerated and possible to crush in low energy milling device.

The method of the invention is suitable for adding different additives (e.g. promoters in the case of catalyst, or other elements for other purposes) before decomposition. One way to decompose this solution to metal oxide(s) is continuously dripping the stock solution into a rotary kiln. The temperature in the rotary kiln may vary between 250–700° C., preferable 350–600° C. An essential feature of the invention comprises utilization of additives selected from organic compounds added to the nitrate stock solution. By adjusting additive quantity and/or temperature in the rotary kiln it is possible to control powder characteristics (phase content/crystalline structure, surface area, particle size, microstructure etc). Without such organic additives, when adding such an additive, the powder will freely run out from the rotary kiln making a continuous process possible. Preferred additives are selected from carbohydrates (glucose, fructose, lactose, sucrose or other saccharides), glycine and carboxylic acid. Moreover, the powder is agglomerated in hard and large lumps. Low quantity or none of these additives results always in $\alpha\text{-Fe}_2O_3$. High quantity of an organic additive results in $\gamma\text{-F}_2O_3$ when the pyrolysis temperature is low.

EXAMPLES

Example 1

Iron was dissolved in nitric acid together with nitrates of the promoters such as Cr, Cu, K and Na in the required proportions and a stock solution was obtained. This solution was dripped at given feed rate into rotary kiln at 350° C. Powder characteristics were measured using XRD analysis and isothermal nitrogen adsorption for specific surface area (according to Brunauer, Emmett and Teller theory). Surface area on synthesised powder (measured by nitrogen adsorption) was 73 $m^2/g$.

Disadvantage: The powder was strong adhered to the rotary kiln walls and very hard particles.

Example 2

The stock solution was prepared similar to Example 1. Then a certain quantity of glucose was dissolved corresponding to the ⅙ of the so-called "stoichiometric ratio" between oxidising (nitrates) and reducing (glucose) reactants. This solution was dripped at given feed rate into a rotary kiln at 400° C.

X-ray analysis resulted in $\alpha\text{-Fe}_2O_3$ with parameters a=5.035 Å, c=13.758 Å and crystallite size $D^{(024)}$=285 Å.

Surface area on synthesised powder (measured by nitrogen adsorption) was about 50 $m^2/g$.

SEM investigation showed a unique microstructure consisting of large porosity with cavities up to 5 $\mu m$. Using atomic-resolution TEM, a homogeneous distribution of Fe, Cu, and Cr was found. In the same time very unusual crystal morphology was observed by TEM examination.

Example 3

The stock solution was prepared similar to Example 1. Then a quantity of glucose was dissolved corresponding to a ratio greater than ½ of the so-called "stoichiometric ratio" between oxidising (nitrates) and reducing (glucose) reactants. This solution was dripped at given feed rate into rotary kiln at 350° C.

X-ray analysis resulted in a cubic $\gamma\text{-Fe}_2O_3$ with parameter a=8.333 Å, and crystallite size $D^{(440)}$=97 Å.

Surface area on synthesised powder (measured by nitrogen adsorption) was 70 $m^2/g$.

Such powders are used in magnetic tape memories.

Example 4

The stock solution was prepared similar to Example 1. Then a certain quantity of glucose was dissolved corresponding to the ½ of the so-called "stoichiometric ratio" between oxidising (nitrates) and reducing (glucose) reactants. This solution is dripped at given feed rate into rotary kiln at 400° C. X-ray analysis resulted in $\alpha\text{-Fe}_2O_3$ and $\gamma\text{-Fe}_2O_3$.

Example 5

A mixture of metallic Co and Fe in the molar ratio 1:1 is dissolved in concentrated nitric acid. Aluminium hydroxide is added to an overall molar ratio of Fe:Co:Al of 1:1:2. Finally $KNO_3$ is added so the molar percentage is 1%.

This solution is dripped at a constant feed rate into a rotating kiln at 350° C.

The powder is crushed, sieved, mixed with graphite and pelletised.

The pellets are calcinated in a conveyor furnace at a temperature of 550° C.

The pellets are reduced in pure hydrogen and are useful as catalyst for both ammonia synthesis and decomposition.

Example 6

A mixture of metallic Cu and Zinc oxide, ZnO, is dissolved in concentrated $HNO_3$. The molar ratio is 1:1. Alumina is added to an overall molar ratio of Cu:Zn:Al of 1:1:1. The slurry is decomposed at 350° C.

The powder is crushed, sieved, mixed with graphite and pelletised.

The pellets are reduced in dilute hydrogen and are useful as catalyst for methanol synthesis or WGS conversion.

What is claimed is:

1. A process for the production of a mixed oxide catalyst with iron oxide and metal oxides selected from one or more of the oxides of Co, Al, Ni, Zn, Cu and Cr, the process comprising the steps of:
    (a) providing a nitric acid solution with iron nitrate and a nitrate of one or more metals of Co, Al, Ni, Zn, Cu and Cr;
    (b) adding to the nitric acid solution a carbohydrate, an amino acid and/or a carboxylic acid;
    (c) decomposing the solution obtained in step (b) at a temperature of between 250 and 700° C. with free air supply to obtain the mixed oxide catalyst containing the iron oxide in its alpha and or gamma form; and
    adding one or more promoters in the form of $PR(NO_3)_x$ to the acid solution of step (a), where PR is chosen from Na, K, Cs, Mg, Ca, Ba, Sr and Rb.

* * * * *